US009291446B2

(12) United States Patent
Schneider et al.

(10) Patent No.: US 9,291,446 B2
(45) Date of Patent: Mar. 22, 2016

(54) OPTICAL COHERENCE TOMOGRAPHY WITH AN EXTENDED DYNAMIC RANGE

(71) Applicant: KARLSRUHER INSTITUT FÜR TECHNOLOGIE, Karlsruhe (DE)

(72) Inventors: Simon Schneider, Welzheim (DE); Christian Koos, Siegelsbach (DE); Wolfgang Freude, Karlsruhe (DE); Juerg Leuthold, Walzbachtal (DE)

(73) Assignee: KARLSRUHER INSTITUT FÜR TECHNOLOGIE, Karlsruhe (DE)

( * ) Notice: Subject to any disclaimer, the term of this patent is extended or adjusted under 35 U.S.C. 154(b) by 58 days.

(21) Appl. No.: 14/371,851

(22) PCT Filed: Jan. 10, 2013

(86) PCT No.: PCT/EP2013/000061
§ 371 (c)(1),
(2) Date: Jul. 11, 2014

(87) PCT Pub. No.: WO2013/107621
PCT Pub. Date: Jul. 25, 2013

(65) Prior Publication Data
US 2015/0049340 A1    Feb. 19, 2015

(30) Foreign Application Priority Data
Jan. 16, 2012   (DE) .................. 10 2012 000 702

(51) Int. Cl.
*G01B 11/02*       (2006.01)
*G01B 9/02*        (2006.01)
*A61B 5/00*        (2006.01)

(52) U.S. Cl.
CPC .......... *G01B 9/02091* (2013.01); *A61B 5/0033* (2013.01); *G01B 9/02049* (2013.01); *G01B 9/02067* (2013.01); *G01B 9/02072* (2013.04);
(Continued)

(58) Field of Classification Search
CPC ................. G01B 9/02091; G01B 9/02083
USPC .................................. 356/497, 479
See application file for complete search history.

(56) References Cited

U.S. PATENT DOCUMENTS 8,744,793 B2 *   6/2014   McKeon ............... G01H 17/00
                                              600/437
2010/0174190 A1  7/2010   Hancock et al.

FOREIGN PATENT DOCUMENTS

WO    2011068862 A2   6/2011

OTHER PUBLICATIONS

International Search Report mailed May 7, 2013 (PCT/EP2013/000061); ISA/EP.

(Continued)

*Primary Examiner* — Jonathan Hansen
(74) *Attorney, Agent, or Firm* — Banner & Witcoff, Ltd.

(57) ABSTRACT

The invention lies in the field of optical metrology and related to optical coherence tomography (OCT). In particular, the invention relates to an apparatus and a method for the depth-dependent adaptation of the dynamic range of an OCT system to the profile of the backscattered power to be measured. The dynamic range of the measuring method can therefore be decoupled from the dynamic range of the analog/digital converter used. The invention is used, in particular, in the characterization of strongly scattering or strongly absorbing biological or technical samples.

10 Claims, 9 Drawing Sheets

(52) U.S. Cl.
CPC .......... *G01B 9/02083* (2013.01); *A61B 5/0066* (2013.01)

(56) References Cited

OTHER PUBLICATIONS

Chang, S. et al. "Attenuation compensation for optical coherence tomography imaging", Optics Communications, Dec. 1, 2009, pp. 4503-4507, vol. 282, No. 23, North-Holland Publishing Co., Amsterdam, NL—ISSN 0030-4018.

Ishikawa, H. et al. "High Dynamic Range Imaging Concept-Based Signal Enhancement Method Reduced the Optical Coherence Tomography Measurement Variability", Investigative Ophthalmology & Visual Science, Jan. 30, 2013, pp. 836-841, vol. 54, No. 1, ISSN 0146-0404.

* cited by examiner

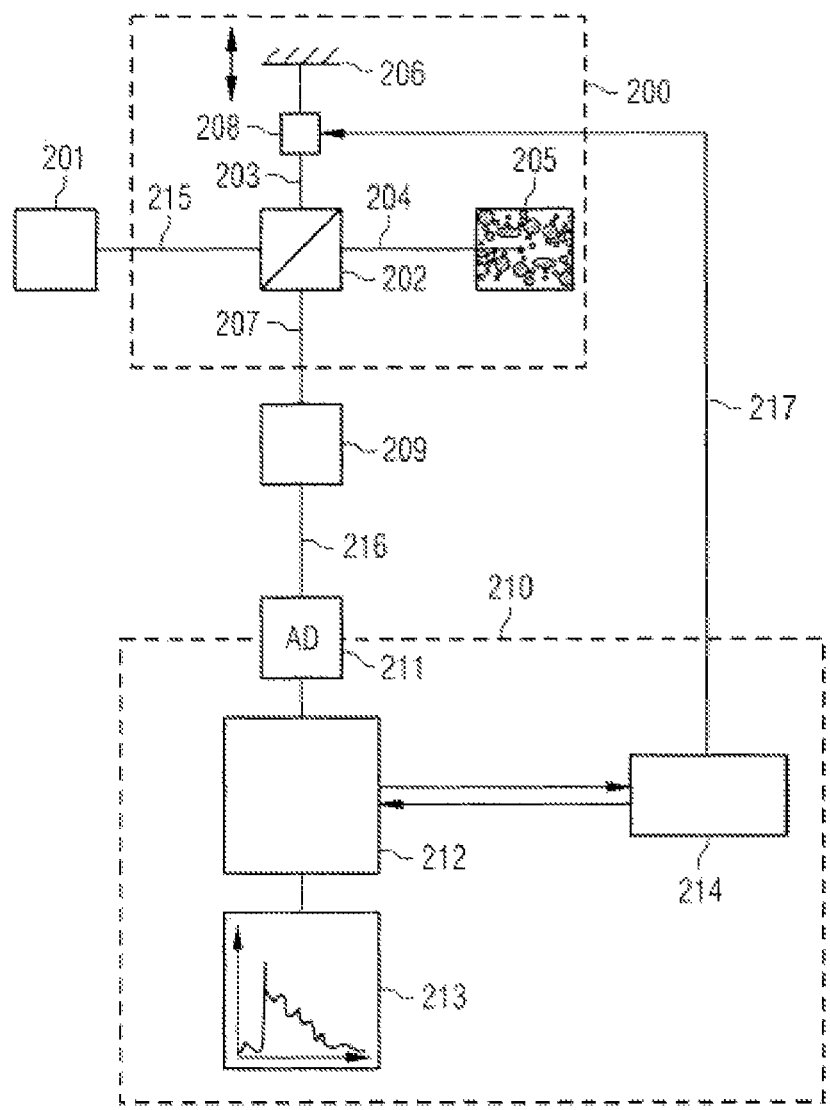

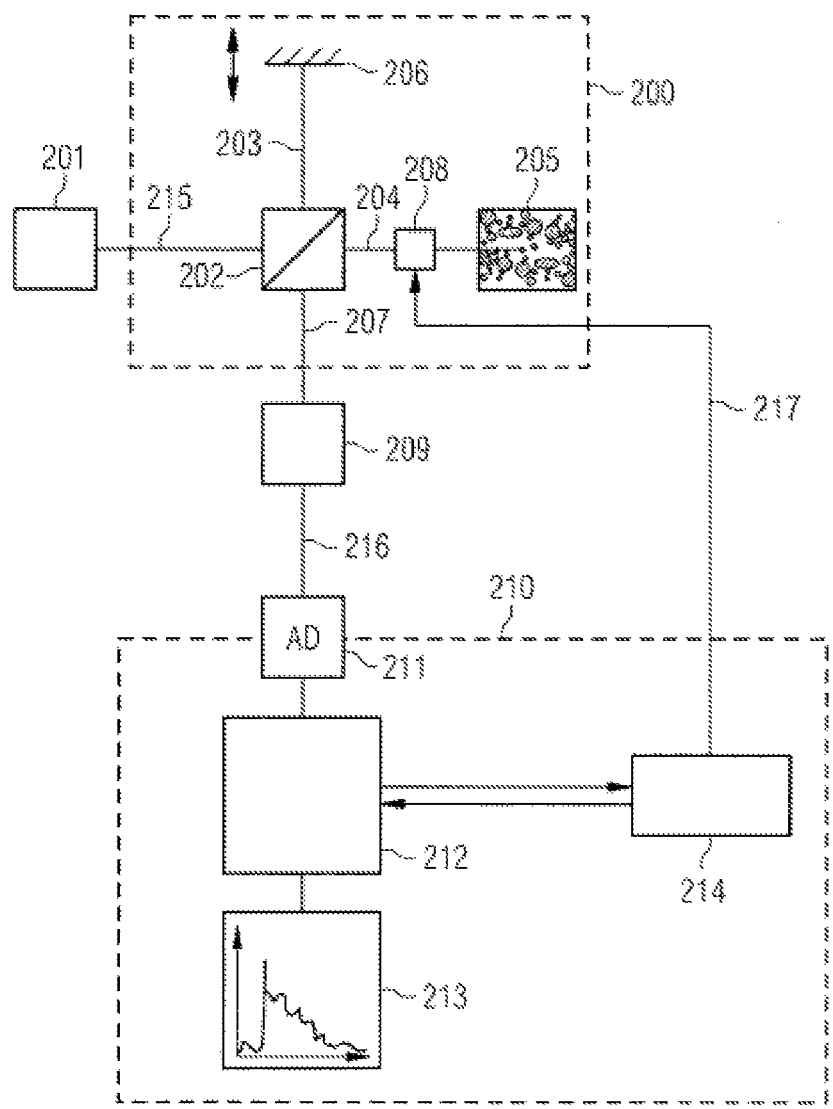

OPTICAL COHERENCE TOMOGRAPHY WITH AN EXTENDED DYNAMIC RANGE

RELATED APPLICATIONS

The present application is a U.S. national stage application under 35 U.S.C. 371 of PCT/EP2013/000061, filed on Oct. 1, 2013, and the present application claims priority to and the benefit of the above-identified application, which is incorporated by reference herein in its entirety.

BACKGROUND

The invention lies in the field of optical metrology and related to optical coherence tomography (OCT). In particular, the invention relates to an apparatus and a method for the depth-dependent adaptation of the dynamic range of an OCT system to the profile of the backscattered power to be measured. The dynamic range of the measuring method can therefore be decoupled from the dynamic range of the analog/digital converter used. The invention is used, in particular, in the characterization of strongly scattering or strongly absorbing biological or technical samples.

Optical coherence tomography is a three-dimensionally imaging method which detects the optical scattering properties in the volume of a sample. OCT allows for spatial resolutions of a few micrometers in all spatial directions and is characterized by its high sensitivity. The areas of application of OCT are primarily in medicine and comprise, for example, tissue examinations in ophthalmology, dermatology, and dentistry. Furthermore, OCT is increasingly applied in materials science and process engineering. OCT systems exist in different embodiments. Widely used embodiments are the time-domain OCT (TD-OCT), first described by Huang et al. in "Optical Coherence Tomography," Science, vol. 254, no. 5035, 1178-1181, November 1991; the spectral-domain OCT (SD-OCT), first described by Fercher et al. in "Measurement of intraocular distances by backscattering spectral interferometry," Elsevier Optics Communications, vol. 117, 42-48, May 1995; and OCT with tunable laser source or swept-source OCT (SS-OCT), first described by Chinn et al. in "Optical coherence tomography using a frequency-tunable optical source," Optics Letters, vol. 22, no. 5, 340-342, March 1997. The invention described herein relates particularly to the TD-OCT and SS-OCT embodiments, even though it is fundamentally not limited to said embodiments.

In OCT, the sample to be examined is irradiated with short-coherent light from a laterally single-mode source. A portion of the light backscattered from the sample is detected in laterally single-mode and brought to interference with the light of the source. The backscatter profile along the exciting light beam is determined with spatial resolution from the temporal coherence of the backscattered light and the emitted light. A three-dimensional depiction is generated by irradiating different points of the sample with the measuring beam and recording the various depth profiles of the backscattered power (so-called A-scans).

For example, a conventional OCT system consists of a Michelson interferometer, comprising an illumination arm, a sample arm, a reference arm, and a detection arm. Each arm can be an optical fiber or have a free beam optical design. The illumination arm contains a light source. The reference arm comprises an optical path and a reference reflector. The sample arm comprises an optical path and a focusing measuring head. The detection arm contains a photodetector. If a differential detection principle is applied, the illumination arm preferably performs the additional task of a second detection arm. For such purpose, the optical power is decoupled from the illumination arm to the differential detector by means of coupler/beam splitter or circulator.

For conventional TD-OCT, a broadband-emitting light source (e.g. white light) is used. Technical realizations, for example, can be superluminescence diodes (SLD) or short-pulse lasers in conjunction with high non-linear, e.g. microstructured, optical fibers. For detecting the coherence properties, the path length of the reference arm is modified by shifting the reference reflector. Backscattering along the measuring beam generates characteristic interference patterns which are recorded as function of the position of the reference reflector. This allows for the measurement of backscattering from different sample depths. A depth scan of the reflectivity profile thus obtained from a point in the sample is commonly called "A-scan." The interference pattern on which the A-scan is based is available in the form of an analog electrical signal at the outlet of the photodetector. It is detected and digitally analyzed by an analog/digital converter ("AD converter").

Similar to the TD-OCT, a conventional SD-OCT also has a broadband-emitting light source. However, the length of the reference arm for an SD-OCT is constant. The interference light is detected spectrally separate and the generating wavelength-dependent interference patterns are analyzed. For such purpose, an optical grid is frequently fitted on the detector side which images the different spectral portions onto a detector cell. The power on the individual detectors is read by means of an AD converter and further digitally processed. The depth-resolved backscatter intensity profile (A-scan) of the sample can be calculated by means of a numerical Fourier transformation.

The light source for conventional SS-OCT is a narrowband laser which is quickly adjusted over a large frequency band. The interference pattern is detected as a function of the optical frequency. The thus resulting analog electrical measuring signal is recorded after detection by means of analog/digital conversion and subjected to a numerical Fourier transformation. This results in a depth-resolved backscatter intensity profile (A-scan) of the sample.

The interferometric measuring method allows for highly sensitive, coherent detection of the light backscattered from the sample. In "In vivo ultrahigh-resolution optical coherence tomography," Optics Letters, vol. 24, no. 17, 1221-1223, September 1999, Drexler et al. describe a time-domain OCT (TD-OCT) with differential detection, which is provided with a bandpass filter and an amplifier between detector and data acquisition. The filter is designed as a second-order Butterworth filter. It causes a suppression of noise components in the signal and thus allows for an increase of the measuring sensitivity.

In "Signal post processing in frequency domain OCT and OCM using a filter bank approach," Photonics West, Proc. SPIE Int. Soc. Opt. Eng., page 644300-6, January 2007, Hofer at al. describe a frequency domain OCT system with a digital filter downstream of the detector array. The filter is used for compensation of the frequency-dependent decrease of the signal strength caused by the lateral expansion of the single detectors. The paper describes a numerical filtering downstream from an A/D converter.

However, in all these methods, particularly with strongly scattering or absorbing samples, the backscatter signal frequently decreases greatly with depth. The delimited dynamic range of conventional measuring systems thus also delimits the measurable depth. This, for example, is a problem when examining samples with a backscatter signal from the volume which is significantly weaker than the portion originating from the sample surface. Small signal portions which originate predominantly from deeper layers of the sample are no longer detectable due to a delimited dynamic range.

Therefore, the problem addressed by the invention is that of expanding the usable measuring depth of optical coherence tomography. This problem is solved by a system and a method for optical coherence tomography and a computer-implemented method and a computer system for controlling an optical coherence tomography measurement with the features in the independent claims. Preferred embodiments are subject matter of the dependent claims.

BRIEF DESCRIPTION OF THE DRAWINGS

These and other objects, features, aspects, and advantage of the present disclosure will become better understood with regard to the following description, claims, and drawings. The present disclosure is illustrated by way of example, and not limited by, the accompanying figures in which like numerals indicate similar elements.

FIG. 2 shows a schematic structure of a system according to a first preferred embodiment of the disclosure.

FIG. 3 shows a schematic structure of a system according to a second preferred embodiment of the disclosure.

DETAILED DESCRIPTION

Figure 1A:
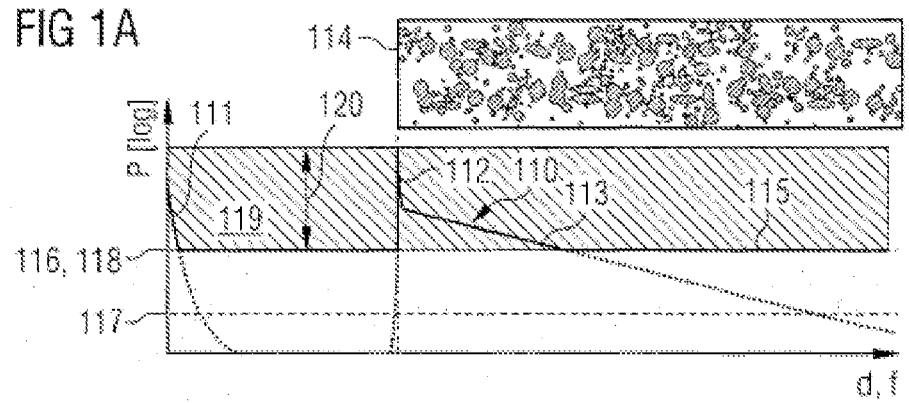
FIGS. 1A-1D show exemplary signal profiles to illustrate a preferred effect of a method according to the disclosure on the basis of a comparison to conventional signal profiles.

In one aspect, the invention thus provides a system for optical coherence tomography. This system comprises an optical detection unit for optical detection of a measurement-depth-dependent optical backscatter profile. This detection unit is particularly designed as interferometric unit, in which a beam generated by a light source is divided into a sample beam and a reference beam which are subsequently brought to interference. The optical detection unit is designed to generate an analog measuring signal of the detected, measuring-depth-dependent optical backscatter profile. In particular, the analog optical interference signal is converted to an analog electrical measuring signal by means of a photodetector.

A particular aspect of the present invention is the fact that the optical detection unit has a controllable, i.e. adjustable (adaptive) analog signal processing unit which is designed to selectively weight the portions of the analog measuring signal pertaining to the different measuring depths on the basis of a detected control signal. Weighting in this context denotes amplification or weakening of specific signal components in the measuring signal as compared to other signal components in the measuring signal.

Depending on the applied method of optical coherence tomography, the different measuring depths of the backscatter profile are represented by different components of the analog measuring signal. For example, in a TD-OCT measurement, the analog measuring signal represents, at different times, different measuring depths while, for example, in an SS-OCT measurement, different frequency components of the analog measuring signal represent different measuring depths. Thus, the adaptive analog signal processing unit is designed correspondingly, e.g. to temporally selectively weight (weaken or amplify) the analog measuring signal or to specifically selectively weight different frequency components. The selection and weighting of the individual measuring depths is preferably determined precisely by means of the control signal. The control signal thus determines the adjustable function of the signal processing unit. This can be a selection from a multitude of discrete predetermined configurations or a determination from a continuously changeable configuration.

Furthermore, the system comprises a signal converter unit which is designed to detect the analog measuring signal of the optical detection unit and convert it to a digital signal which is thus also considered to be a digital measuring signal. The signal converter unit thus acts as analog/digital converter. The system further comprises a data acquisition and processing unit which is designed to determine whether a dynamic range of the signal converter unit is exceeded or falls short. The data acquisition and processing unit is further designed to control the analog signal processing unit by means of the control signal such that the determined dynamic range of the single converter unit which exceeded or fell short is counteracted. Insofar as specific signal components of the analog measuring signal are, at specific measuring depths, outside of the dynamic range of the signal converter unit due to particularly strong or particularly weak backscatter from a sample to be examined, these signal components are appropriately weighted by the adaptive analog signal processing unit, i.e. dampened or amplified, in order to counteract the determined dynamic range which was exceeded or fell short. Preferably, signal components which are too weak are thus amplified and/or signal components which are too strong are weakened.

The influence of the signal processing unit thus results in a modified measuring signal which is preferably within the dynamic range of the signal converter unit. In particular, the modified analog measuring signal has preferably a lower dynamic than the unmodified signal. The modified analog measuring signal also no longer exactly reflects the backscatter characteristics of the sample to be examined but is changed or distorted by the influence of the signal converter unit, wherein this change or distortion is known and specifically controlled particularly by the control signal. After the modified analog signal is digitalized by means of the signal converter unit, the modified digital signal also no longer exactly reflects the backscatter characteristics of the sample to be examined. In order to compensate, data acquisition and processing unit is designed to correct the digital signal generated by the signal converter unit such that the weighting of different signal portions by the signal processing unit is compensated. Since the influence of the data acquisition and processing unit, which is controlled by the control signal, on the analog measuring signal is known, compensation on the digital side is possible.

Ultimately, a digital signal is provided which corresponds to an undistorted analog signal which would result from an analog signal without the analog signal processing unit with a hypothetical signal converter unit with unlimited dynamic. Therefore, analog signals can be detected and converted to digital signals, the dynamic of which is greater than the dynamic range of the signal converter unit. This results in an expansion of the usable measuring depth of the optical coherence tomography even for samples which strongly reflect on the surface, and for samples, the backscatter of which greatly decreases with depth, which, for example, are thus greatly absorbent.

The problem addressed by the invention is thus solved by the use of an adaptive analog signal processing unit according to the invention, which allows for a weighting of the portions of the analog measuring signal pertaining to the different depths. The term "analog measuring signal" denotes, e.g. an electrical signal. Weighting can be an amplification or damping of the corresponding signal portions. As will be further described in detail in the following by means of examples of preferred embodiments, said weighting can be optical or analog/electrical. Due to the weighting, the constant dynamic range of the A/D converter is imaged onto a depth-dependent variable dynamic range for the backscatter measurement.

By way of the use of an adaptive signal processing unit, a separate sensitivity profile, which is specially adapted, i.e., location-dependent, along the vertical measurement direction (measurement depth) can be implemented, in particular automatically, for example, for each lateral position of a sample to be studied.

In a preferred embodiment, the optical detection unit comprises a narrowband light source (in particular a variable frequency laser source), the wavelength of which is variable over time within a scanning range of the optical detection unit. The spectral width of the light source is thus substantially smaller than the spectral width of the scanning range in this case. In particular, the system is therefore preferably a swept-source OCT system. In addition, the optical detection unit preferably comprises an optical detector, which is designed to convert an optical signal of the optical detection unit (in particular an optical interference signal) into an analog electrical measurement signal. In this embodiment, the analog signal processing unit preferably comprises an adaptive (in particular linear) time-invariant filter, which performs filtering of the electrical measurement signal. In particular, filtering of the analog electrical measurement signal generated by the optical signal is therefore performed, to generate the analog measurement signal generated by the optical detection unit.

The adaptive analog signal processing unit is therefore an electrical signal processing unit in this preferred embodiment. It is designed in this case to perform spectral adaptive filtering of the electrical signal of the optical detector (photodetector), i.e., to damp or amplify different frequency components differently and therefore to weight them differently. The signal processing unit can comprise appropriate passive and/or active filter components for this purpose. In this case, the spectral filter property of the electrical signal processing unit, i.e., in particular the selection and/or setting of the filter components, is controllable by means of the control signal. Depending on the control signal, a specific spectral filter characteristic of the signal processing unit can thus be set continuously or discretely, which then remains unchanged during the measurement over the entire measurement depth to be studied. If the dynamic range of the A/D converter is still overshot during a measurement over the desired or fundamentally achievable measurement depth, the filter characteristic of the signal processing unit is preferably further adapted by means of a corresponding control signal.

Furthermore, the adaptive filter preferably comprises a high-pass filter (in particular the transmission of the filter continuously increases with the frequency) and/or a bandpass filter (in particular for selection of a specific depth range) and/or a notch filter (in particular in the form of a bandstop filter for suppressing strong backscattering peaks at the sample surface) and/or a broadband amplification unit (in particular to, inter alia, weight the lesser signal fractions more strongly at greater measurement depths, while other signal fractions can be damped or suppressed by means of further filter components). The composition and/or the frequency ranges and/or the extent of the amplification or damping can be established in discrete steps or continuously by the control signal in this case.

In a further preferred embodiment, the optical detection unit comprises an optical interferometer having a sample arm and a reference arm, wherein an optical path difference between the sample arm and the reference arm is chronologically variable to scan the measurement depth. The system preferably uses the principle of a time-domain OCT measurement in particular, during which, for example, a reference reflector provided in the reference arm is varied in its position in the axial direction of the reference arm to scan the measurement depth. In this case, the analog signal processing unit preferably comprises a chronologically variable (preferably linear) amplification and/or damping member, which is controlled by the data acquisition and processing unit in dependence on (i.e., synchronously to) the optical path difference between the sample arm and the reference arm (i.e., in particular the position of the reference reflector). A separate weighting of the measurement signal is therefore achieved for each measurement depth.

The adaptive analog signal processing unit can be implemented in this case in various ways. In a preferred embodiment, it is in this case an analog electrical signal processing unit, which acts in particular directly on the analog electrical signal generated by an optical detector (photodetector), before it is digitized by means of the signal converter unit. For this purpose, the adaptive analog signal processing unit preferably comprises an electrical amplification and/or damping member.

In another preferred embodiment, the adaptive analog signal processing unit only acts indirectly on an analog electrical signal generated by an optical detector (photodetector), for example, in that it acts directly on at least a part of the optical signal before it is acquired by the optical detector. In this preferred embodiment, it is therefore in particular an analog optical signal processing unit, which comprises in particular an optical amplification and/or damping member.

In this case, the optical amplification and/or damping member can be arranged at various points of an optical light guide (in particular beam guide) and can therefore act on various sections of the optical light guide. In a preferred embodiment, the optical amplification and/or damping member is thus arranged in the sample arm of the optical interferometer. In another preferred embodiment, the optical amplification and/or damping member is arranged in the reference arm of the optical interferometer. In a further preferred embodiment, the optical amplification and/or damping member is arranged in a detection arm of the optical interferometer, in which light from the sample arm and from the reference arm interfere.

In a further aspect, the invention provides a method for optical coherence tomography, which comprises an acquisition of a measurement-depth-dependent optical backscattering profile by means of an optical detection unit. In this case, an analog measurement signal of the acquired measurement-depth-dependent optical backscattering profile is generated. This analog measurement signal is converted by means of a signal converter unit into a digital signal. In addition, the method comprises an ascertainment of an overshoot and/or undershoot of a dynamic range of the signal converter unit and selective weighting (damping and/or amplification) of the fractions, which are associated with various measurement depths, of the analog measurement signal, by means of an adaptive analog signal processing unit such that an ascertained overshoot and/or undershoot of the dynamic range is counteracted. The weighting is performed selectively in that the influence on different signal components can differ in a targeted manner depending on the ascertained overshoot and/or undershoot of the dynamic range, i.e., some signal components can be attenuated or amplified more or less, depending on which measurement depth they represent.

In addition, the method comprises a correction of the digital signal such that the weighting of various fractions of the analog signal in the digital signal, which is performed by means of the analog signal processing unit, is thus compensated for.

The acquisition of the optical backscattering profile, the generation of an analog measurement signal, and the ascertainment of an overshoot and/or undershoot of the dynamic range are preferably firstly carried out for a first setting of the adaptive analog signal processing unit. Subsequently, in dependence on the acquired overshoot and/or undershoot of the dynamic range, an adapted setting of the adaptive analog signal processing unit is performed and the acquisition of the optical backscattering profile, the generation of an analog measurement signal, and the ascertainment of an overshoot and/or undershoot of the dynamic range are carried out again using the adapted setting. If an overshoot and/or undershoot of the dynamic range is still encountered, the control loop is preferably repeated using a setting of the analog signal processing unit, which is adapted in each case until a predefined interrupt criterion is met. The correction of the digital signal is subsequently performed according to the last setting of the analog signal processing unit.

Preferably, a short coherence optical measurement method is thus provided for the highly-dynamic acquisition of a location-dependent backscattering profile with the aid of an optical measurement and detection unit, which outputs an analog measurement signal, an analog-digital converter, an adaptive analog signal processing unit, and a data acquisition and processing unit, which comprises the following steps:

1. Recording the measurement data of a backscattering profile using a first setting of the adaptive analog signal processing unit,
2. Evaluating the measurement data by way of the data acquisition and processing unit,
3. Analysis of the data with respect to overshoot of the upper (overshoot) and lower (undershoot) limits of the dynamic range,
4. Derivation of an adapted signal processing guideline for the adaptive signal processing unit,
5. Recording of the measurement data of a backscattering profile using the adapted setting of the adaptive analog signal processing unit,
6. Iterative repetition of steps 2-5 until a predefined interrupt criterion is fulfilled,
7. Numeric (digital) compensation of the influence of the adaptive analog signal processing on the measurement data,
8. Outputting the location-dependent backscattering profile, which is acquired in a highly-dynamic manner.

In a further aspect, the invention offers a computer-implemented method for controlling an optical coherence tomography measurement, comprising acquiring a digital signal (digital measurement signal), which is generated by a signal converter unit, of a measurement-depth-dependent backscattering profile of an optical coherence tomography measurement;

ascertaining an overshoot and/or undershoot of a dynamic range of the signal converter unit (for example, by succession of a predefined minimum number of digital values in a predefined value range);

generating a control signal for controlling an adaptive analog signal processing unit such that a selective weighting, which is caused by the control signal of the adaptive analog signal processing unit, of analog signal fractions, which are associated with various measurement depths, of the backscattering profile of the optical coherence tomography measurement counteracts the ascertained overshoot and/or undershoot of the dynamic range; and correcting the digital signal such that the selective weighting, which is performed by the signal processing unit, of various signal fractions is compensated for.

To generate a suitable control signal, preferably a computer readable and computer processable control guideline is firstly provided, which establishes a relationship between overshoots and/or undershoots of the dynamic range and the control signal to be generated (for example, in the form of a formula). This predetermined and stored relationship is applied to an ascertained overshoot and/or undershoot of the dynamic range and provides as a result the control signal to be generated. The stored relationship reflects in this case the optical or electrical damping and/or amplification properties of the analog signal processing unit and the dependence thereof on the control signal. Thus, for example, if a specific frequency or a specific frequency range of the analog measurement signal is to be damped or amplified, to avoid a specific infringement of the dynamic range, the control guideline establishes a control signal suitable for this purpose. In particular, the control guideline is stored in a databank.

In a further aspect, the invention provides a computer system for controlling an optical coherence topography measurement, comprising:

a digital signal input for acquiring a digital signal (digital measurement signal), which is generated by a signal converter unit, of a measurement-depth-dependent backscattering profile of an optical coherence tomography measurement;

a data evaluation unit for ascertaining an overshoot and/or undershoot of a dynamic range of the signal converter unit;

a data memory having a control guideline, which, for overshoots and/or undershoots of the dynamic range of the signal converter unit, establishes values for controlling an adaptive analog signal processing unit such that a selective weighting, which is caused by the control signal of the adaptive analog signal processing unit, of analog signal fractions, which are associated with various measurement depths, of the backscattering profile of the optical coherence tomography measurement counteracts the overshoots and/or undershoots of the dynamic range; and a control module, which generates a control signal the ascertained overshoot and/or undershoot of the dynamic range according to the control guideline stored in the memory, wherein the data evaluation module is designed to correct the digital signal such that the selective weighting of various signal fractions, which is caused by the signal processing unit according to the control guideline for the generated control signal, is compensated for.

The computer system is preferably designed to execute and/or control one of the methods described here. In a preferred embodiment of a system according to the invention for optical coherence tomography, the data acquisition and processing unit comprises a computer system for controlling an optical coherence tomography measurement according to the invention, in particular according to one of the preferred embodiments described here.

In the case of TD-OCT, the observed backscattering depth is determined by the position of the referenced reflector. The weighting according to the invention of the analog measurement signal is preferably coupled in this case to the position of the referenced reflector. For example, it can be performed by a chronologically variable electrical amplification or damping member. Alternatively or additionally, chronologically variable optical amplification or damping members can be used.

In the case of SS-OCT, scattered light fractions from various depths are imaged on various frequency components of the electrical measurement signal. A depth-selective weighting of the measurement signal can thus be achieved, for example, by filtering of the analog electrical signal using a linear time-invariant filter (linear, time-invariant, LTI).

In both methods, the influences of the analog signal processing are corrected again in a digital processing step. In an iterative method, the weighting guideline (signal processing guideline) is preferably adapted to the shape of the backscattering profile to be measured. Therefore, backscattering profiles may be acquired, the power variations of which are greater than the dynamic range of the A/D converter.

In FIG. 1A to FIG. 1D, the mode of operation of the measurement system and the measurement method are explained on the basis of a preferred embodiment. In this case, an exemplary A-scan 110 is shown as a logarithmic profile of the backscattering profile P over the depth d, which, in SS-OCT systems, is directly linked to the superposition frequency f of the respective spectral component in the interference signal. This backscattering profile P is composed of various signal regions: a strong signal peak 112 usually occurs at the position of the sample surface, followed by an exponentially decreasing profile of the backscattering 113 with increasing penetration depth into the sample 114, which corresponds at greater sample depths to the lower limit 116 of the measurement range, which results in a signal lower limit 115, which no longer reflects the actual characteristic of the signal intensity, which decreases further with increasing sample depth (measurement depth). In the case of SS-OCT, low-frequency fractions and steady fractions in the interference signal result in a strong increase 111 of the reconstructed backscattering profile at the left edge of the measurement range.

In the case of the conventional recording of an A-scan, the lower limit 116 of the measurement range 119 is generally defined by the strongest backscattering occurring within the A-scan and the quantification depth of the A/D converter: The maximum backscattering signal must still lie within the quantification range of the A/D converter. In the case of predefined dynamic range 120 of the A/D converter (typically <72 dB), the level 118 of the (numeric) quantification noise is therefore also predefined. Weak fractions of the backscattered power from deep regions of the sample are thus overlapped by the quantification noise 118 of the A/D converter, although a sensitivity limit 117 of the system, which is defined in principle by the noise of the analog signal, is not yet reached. The noise of the analog signal includes in particular shot noise of the optical detection process and/or thermal noise of the analog electronics and determines the fundamental achievable sensitivity of the system.

Corresponding to this invention, a defined manipulation of the analog measurement signal is now carried out by an analog signal processing unit, which results in a depth-selective weighting. This weighting can be linear or nonlinear. Thus, in particular in this case it can be amplification for greater depths (greater distances from the surface) or attenuation for lesser depths (close to the surface). In general, a weighting guideline 124 is selected in particular so that signal fractions from weakly scattering regions are amplified in relation to those from strongly scattering sections.

Figure 1B:
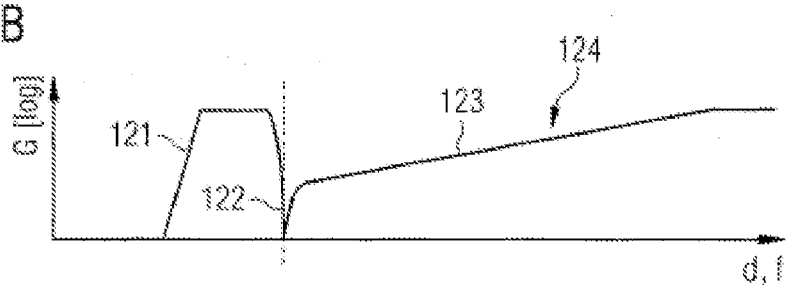
Figure 1C:
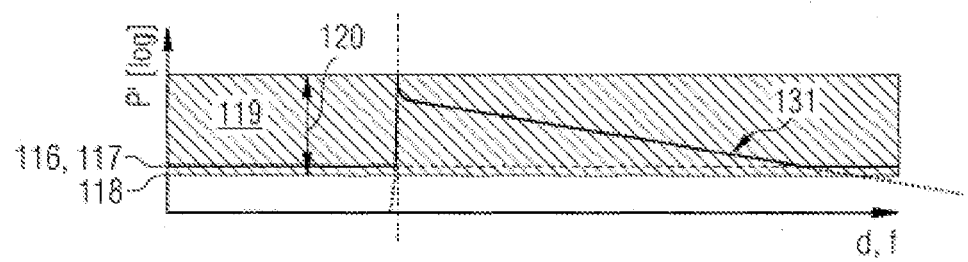

In the case of an implementation as a TD-OCT system, the characteristic may be achieved by means of a chronologically variable amplification or damping member. In the case of an implementation as an SS-OCT system, various spectral filters in the form of adaptive linear time-invariant systems can be used. The profile of the weighting guideline 124 over the depth d preferably behaves essentially inversely in this case to the expected profile of the backscattering profile. FIG. 1B illustrates an example of a weighting guideline G(d) according to a preferred embodiment. In the identified example, the filter contains a high-pass range 121, a notch filter 122, and a high-pass characteristic 123, which increases exponentially with the frequency.

A modified backscattering profile P' 131 is generated by the optional iterative optimization of the signal processing guideline for the analog measurement signal and the adaptation linked thereto of the depth-dependent weighting guideline G(d) (FIG. 1C), said profile being freed of interfering variables (for example, the increase 111 at the left side of the measurement range) and the profile of which being adapted in the available dynamic range 119 of the A/D converter. By way of the leveling of the signal level linked thereto within the A-scan, the level 118 of the (numeric) quantification noise can be lowered below the fundamental noise limit 117 of the analog system. The lower limit 116 of the measurement range is given in this case by the fundamental sensitivity limit 117 of the measurement system.

Figure 1D:
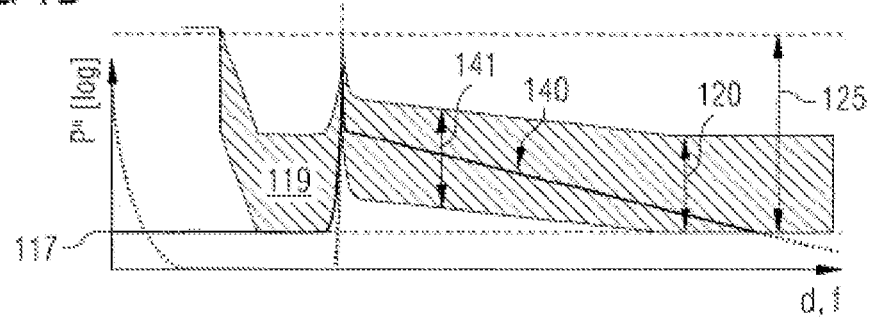

Using this method, A-scans can thus be recorded, in which very strong and very weak scattering powers occur similarly. The modification of the backscattering profile caused by the analog signal processing is subsequently compensated for again numerically in the digital phase. In the case of this correction, system-related interfering variables, for example, the increase 111 at the left side of the measurement range of an SS-OCT, are eliminated. In FIG. 1D, P''' identifies an exemplary reconstruction of the actual backscattering profile 140 after the numeric correction of the depth-dependent weighting.

This reconstruction is an unambiguous imaging guideline, which images the measurement range 119 of the A/D converter on a depth-dependent measurement range 141 of the overall system. Within this measurement range, backscattering profiles can be acquired using a dynamic range 125, which is no longer limited by the dynamic range 120 of the A/D converter.

The advantage of this invention is that by way of the depth-selective weighting of the analog measurement signal, a depth-dependent profile of the acquirable measurement range can be defined, which is adapted to the shape of the backscattering profile (110, 140) to be measured. The term "backscattering profile" identifies in this case the profile of the backscattered optical power P, which is detected by the system, as a function of the depth d. By way of the depth-selective weighting, backscattering profiles may be acquired, the power variations of which are greater than the dynamic range (120) of the A/D converter. The invention therefore allows the complete sensitivity range of an OCT system to be used and therefore scattering events in strongly scattering and absorbent media to be detected at a greater depth.

Thus, for example, backscattered signal fractions may be acquired, which have experienced attenuations of greater than 120 dB in the sample in relation to the incident light. The acquirable dynamic range of the scattered light measurement is determined, inter alia, by the effective quantification depth of the A/D converter, which is typically between 9 and 12 bits and includes noise and harmonic distortions in the converter. This corresponds to a dynamic range between 58 and 72 dB. Within an A-scan, this corresponds to the ratio of the maximum to the minimum signal amplitude.

Preferred embodiments of systems according to the invention are described separately hereafter on the basis of preferred implementations as TD-OCT systems and SS-OCT systems. A corresponding method is applicable in an analogue manner in this case to both possible cases of exemplary implementations.

Figure 4:
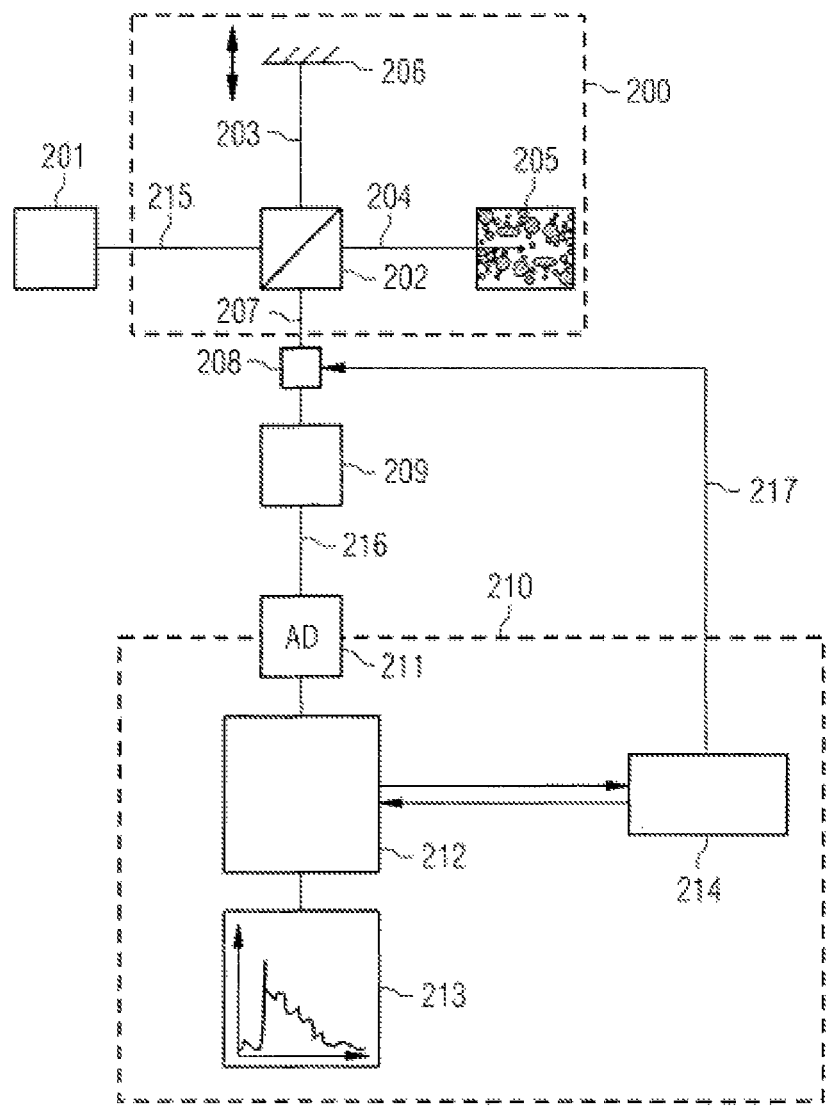
FIG. 4 shows a schematic structure of a system according to a third preferred embodiment of the disclosure.

In the case of TD-OCT, the weighting according to the invention of the analog measurement signal is preferably coupled to the position of the referenced reflector. This is implemented, for example, in one or more of the preferred arrangements described hereafter. The preferred embodiment described hereafter (FIG. 2 to FIG. 4) is based on an OCT system on the basis of a Michelson interferometer 200, wherein the invention can also be implemented in other interferometer arrangements, however.

Light in a broadband light source 201, in particular a white light source, which is arranged in an illumination arm 215, is allocated by a beam splitter 202 onto a reference arm 203 and a sample arm 204, wherein a sample 205 to be studied can be arranged in the sample arm. A reference reflector 206 is arranged in the reference arm 203, which reflects the incident reference light back to the beam splitter 202. The position of the reference reflector is variable along the beam direction of the reference light in this case in a controlled manner such that the optical path difference between the reference light guided in the reference arm 203 and the sample light guided in the sample arm 204 is thus variable.

Backscattered light from the sample 205 interferes in the beam splitter 202 and in a detection arm 207 of the system with light reflected back from the reference reflector 206 and is subsequently incident on the detector 209 (photodetector), which preferably converts the optical signal into an electrical signal in the form of an analog measurement signal 216.

For the digital further processing, storage, and display of the measurement results, the measurement system comprises a data acquisition and processing unit 210, which is designed to acquire the analog measurement signal 216 (in particular as a voltage signal) by means of an analog/digital converter (A/D) 211 and to digitize it in quantified form. The A/D converter 211 preferably has a quantification depth in the range from approximately 8 bits to approximately 16 bits, particularly preferably in the range from approximately 12 bits to approximately 16 bits. In the data acquisition and processing unit 210, the digital signal is subsequently digitally processed by means of a data evaluation module 212, in order to finally be able to output it via a data output unit 213 (for example, in the form of a display screen).

In the preferred embodiment of FIG. 2, an adaptive analog signal processing unit 208 is located in the reference arm 203. This unit functions in particular as a variable optical damping member. Since the reference light is used for the amplification of the measurement signal, optical damping in the reference arm results in attenuation of the analog interference signal, which is supplied to the A/D converter 211. In a corresponding manner, amplification in the reference arm results in amplification of the analog interference signal and therefore also amplification of the electrical signal 216. In the preferred embodiment shown in FIG. 3, an adaptive analog signal processing unit 208 is located in the sample arm 204 and functions as a variable optical damping member, which acts directly on the optical power backscattered from the sample 205. In the preferred embodiment shown in FIG. 4, a variable optical damping member is arranged as an adaptive analog signal processing unit 208 in the detection arm 207 before the detector 209. In this case, signal light and reference light are damped or amplified equally. In the preferred embodiment shown in FIG. 5, the adaptive analog signal processing unit 208 is located between detector 209 and the analog/digital converter (A/D converter) 211 and functions as a variable electrical amplification and/or damping member.

The above-described arrangements may also be transferred similarly to other OCT systems. These include, for example, configurations on the basis of Mach-Zehnder interferometers or systems having differential optical detection. Combinations of the arrangements outlined in FIGS. 2 to 5 are also possible, in which a depth-dependent weighting of the analog measurement signal is achieved by interventions at multiple points of the optical and/or electrical signal path.

The analog signal processing unit 208 preferably changes its damping properties multiple times during a depth scan (A-scan). This can occur continuously and/or at discrete times. To achieve sufficient adaptability, in the case of a chronologically discrete adaptation, the optical damping is preferably changed at least 5 times, particularly preferably at least 20 times during a depth scan.

Figure 5:
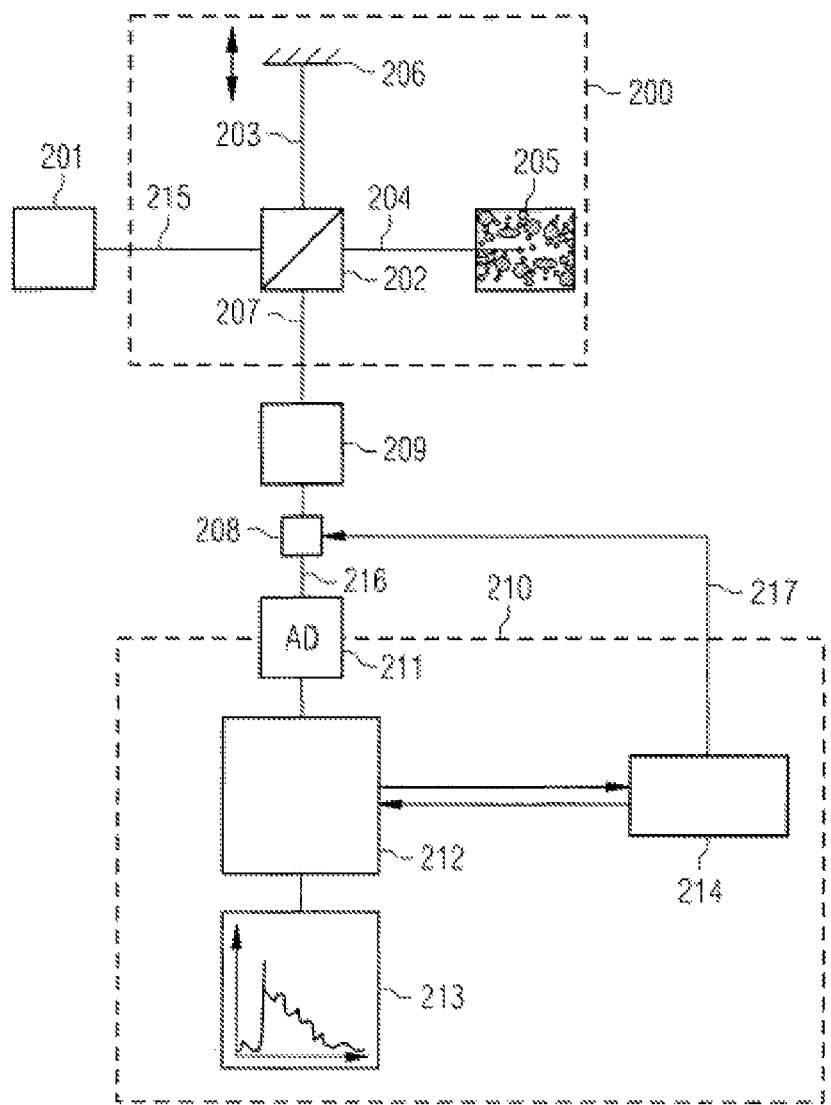
FIG. 5 shows a schematic structure of a system according to a fourth preferred embodiment of the disclosure.

The analog electrical signal processing unit 208 used in the arrangement according to FIG. 5 is preferably technically implemented with the use of a variable low-noise amplifier and/or with the use of a low-noise amplifier having downstream variable damping member. The amplifier is preferably a CMOS amplifier or particularly preferably a GaAs-HEMT amplifier. The variable damping member is preferably proposed as a digital stepped damping member, to simplify the control from a measurement computer.

In order to control the analog signal processing unit in an adaptive manner, the data acquisition and processing unit 210 preferably comprises a control module 214, which has a signal connection to the data evaluation module 212 to monitor the reaching of dynamic limits of the A/D converter 211. The data evaluation module 212 is thus designed in particular to study whether the quantified measurement signal overshoots or undershoots the dynamic range of the converter 211, i.e., whether the upper or the lower limit of the dynamic range is overshot. If this is the case, control values, in particular values which establish the measurement depth, in which the range infringement occurs, are transmitted to the control module 214, which, on the one hand, readjusts the analog signal processing unit 208 via a control signal 217 and, on the other hand, controls the data evaluation module 212 such that the digitized signal of the resulting A-scan is corrected such that the influence of the analog signal processing unit 208 in the digitized signal is compensated for, before the signal comes to the display 213. The check of range overshoots of the dynamics of the A/D converter 211 by means of the data evaluation module 212 and a possible readjustment of the effect of the analog signal processing unit 208 by means of the control module 214 via the control signal 217 therefore occur in particular in the form of an adaptive, closed control loop.

Figure 6:
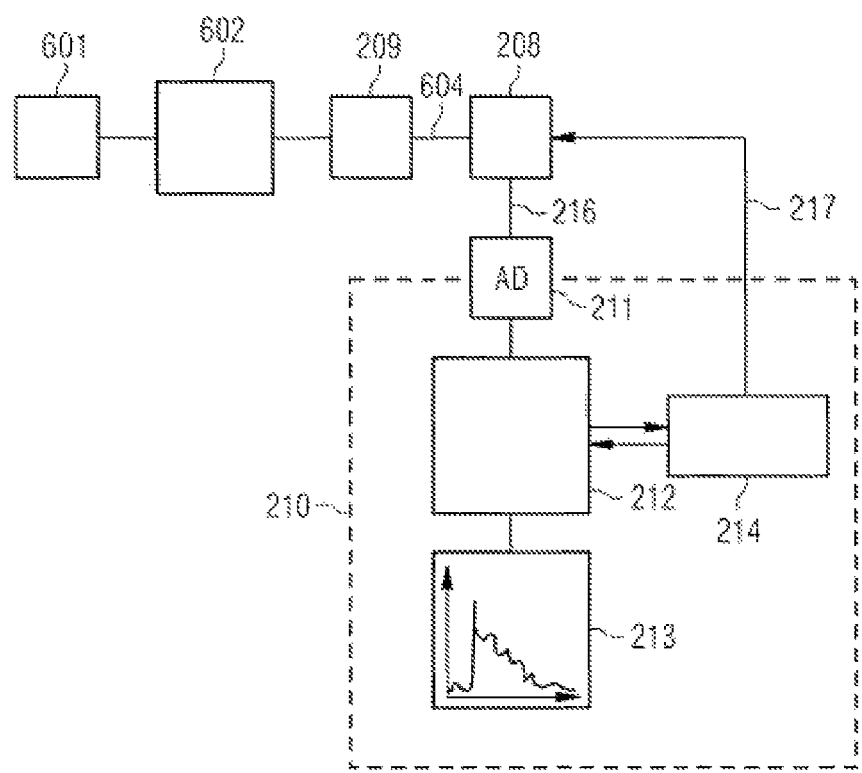
FIG. 6 shows a schematic structure of a system according to a fifth preferred embodiment of the disclosure.

A depth-selective weighting of the measurement signal in the SS-OCT is preferably achieved by filtering of the analog electrical signal using a linear time-invariant filter. A corresponding arrangement according to a preferred embodiment is shown in FIG. 6. Insofar as the same reference signs are used as in the above-described embodiments, the statements thereon may preferably be applied in a similar manner to the embodiment of FIG. 6.

Light of a swept-source laser 601 is coupled into a measurement interferometer 602. This is embodied, for example, as a Michelson interferometer or a Mach-Zehnder interferometer and preferably contains a reference arm, a sample arm, and a sample to be studied. The superimposed light waves from the reference arm and the sample arm enter interference and are received in a quadratic manner in a photodetector 209. The resulting analog electrical measurement signal 604 consists of low-frequency fractions from smaller path length differences, which originate from the scattering at lesser depths, and high-frequency fractions from greater sample depths. These signal fractions are leveled by frequency-selective filtering in an adaptive electric-analog signal processing unit 208.

This signal processing unit 208 is embodied, for example, as a combination of a linear time-invariant filter with a variable amplifier member. The filter can in turn contain multiple cascaded steps. These steps can be, for example, the following systems:

- high-pass filter with a base frequency, which preferably corresponds to twice to ten times the rate at which the A-scans are recorded;
- a tunable notch filter of high quality, which suppresses narrowband contributions of strong scattering events (for example, surface reflections of the sample).
- a high-pass filter with an exponentially increasing transmission characteristics, which compensates for power differences as a result of optical damping within the sample.

The high-pass filter can be embodied, for example, as a first-order or second-order passive LC filter or active Butterworth filter—this ensures a flat phase transition in the transmission range. The filters therefore have a flank steepness of preferably 20 dB to 40 dB per decade. The notch filter is preferably implemented passively as a RC twin-T filter and preferably connected in a Sallen-Key configuration to active components. Furthermore, the use of an active filter component preferably comes into consideration here.

In a further preferred embodiment, the spectral filter is constructed as a filter bank. This can consist of combinations connected in parallel of bandpass filters and damping members. Individual frequency bands may thus be activated in a targeted manner. The individual bandpass filters can in turn be used as passive LC filters or as active components. The variable amplification member can be technically implemented with the use of a variable low-noise amplifier or with the use of a low-noise amplifier with downstream variable damping member. The amplifier is preferably a CMOS amplifier or particularly preferably a GaAs-HEMT amplifier. The variable damping member is proposed as a digital stepped damping member, to simplify the control from a measurement computer in particular by means of the control module 214 of the data acquisition and processing unit 210.

The processed analog signal 216 is then sampled and quantified in the analog/digital converter 211. This converter preferably has a quantification depth in the range from approximately 8 bits to approximately 16 bits, particularly preferably in the range from approximately 12 bits to approximately 16 bits. In the data acquisition and processing unit 210, the digital signal is now preferably subjected to multiple digital processing steps 212, during which the influence of the analog electrical signal processing unit 208 is removed, before the signal comes to the display 213. As already stated above, it is studied in particular in the digital processing step 212 whether the quantified measurement signal overshoots or undershoots the dynamic range of the converter 211. If this is the case, corresponding items of information are transmitted to the control module 214, which readjusts both the analog-digital signal processing unit 208 and also the digital correction in the data evaluation module 212 and in particular triggers the recording of a new A-scan at this point.

Figure 7:
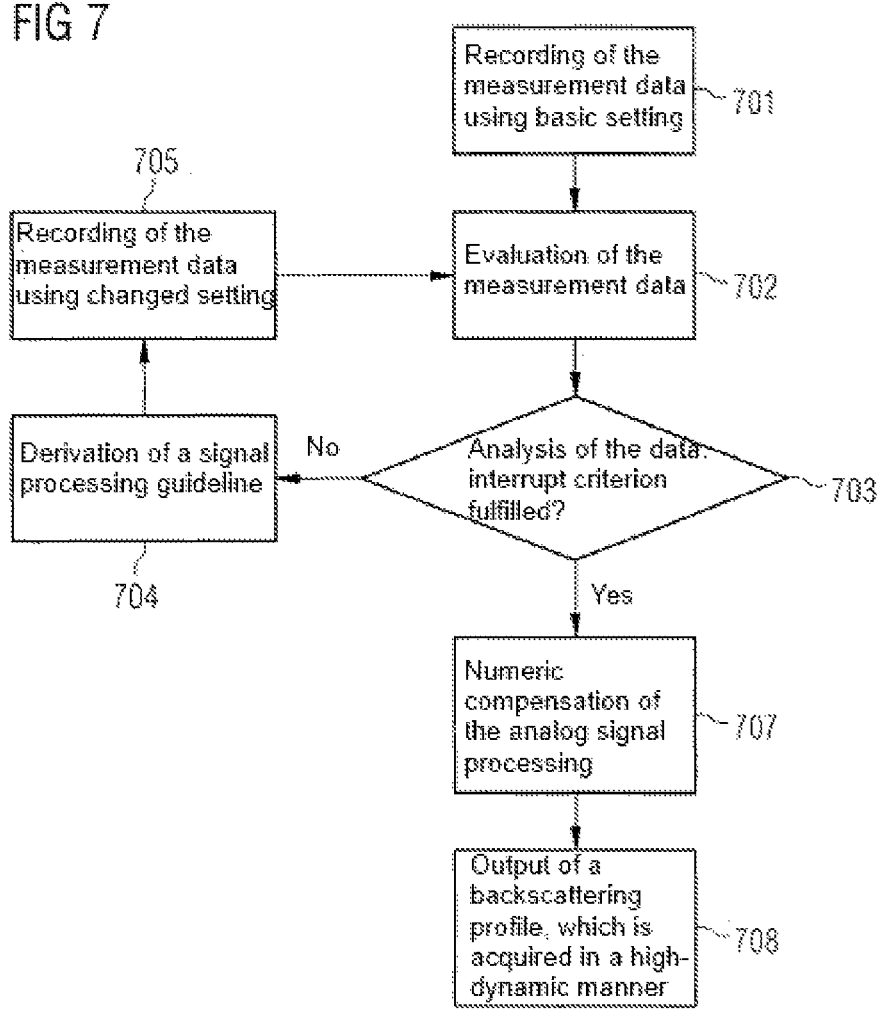
FIG. 7 shows a flow chart to illustrate a method according to a preferred embodiment of the disclosure.

FIG. 7 shows a flow chart to illustrate a method according to a preferred embodiment of the present invention. It is therefore applied in particular to an OCT system having analog signal processing unit (for example, according to FIGS. 2-6), in general causes the decoupling of the overall dynamic range of a depth backscattering measurement (A-scan) from the dynamic range of the A/D converter 211, and therefore enables an expansion of the dynamic range of the measurement.

The illustrated method comprises in particular the following steps:

701. Recording of an A-scan using a first setting of the analog signal processing unit. The recording therefore preferably includes a depth scan of the reference reflector in the case of TD-OCT or a frequency scan of the swept-source laser in the case of SS-OCT, and a conversion into an analog electrical measurement signal and the analog/digital conversion thereof.

702. Digital signal processing of the measurement data and ascertainment of the depth-dependent intensity profile.

703. Studying of the depth-dependent intensity profile for infringement of the dynamic range of the analog/digital converter.

704. If the dynamic range was locally infringed, for example, by overshooting the voltage measurement range or by undershooting the smallest quantification step, a second setting of the analog signal processing unit is ascertained, which counteracts the range infringements.

705. Repeated recording of a further A-scan under the influence of the changed parameters for the analog signal processing unit.

706. Iterative repetition of steps 702-705, until an interrupt criterion is fulfilled in step 703. This can include a noninfringement of the dynamic range of the converter or the reaching of technical limits of the system components.

707. Numeric (digital) compensation of the influence of the adaptive analog signal processing to the measurement data.

708. Output/storage/evaluation of the location-dependent backscattering profile which is acquired in a highly-dynamic manner.

One exemplary embodiment is described in each case hereafter for an SS-OCT and a TD-OCT for the sake of completeness.

Figure 8:
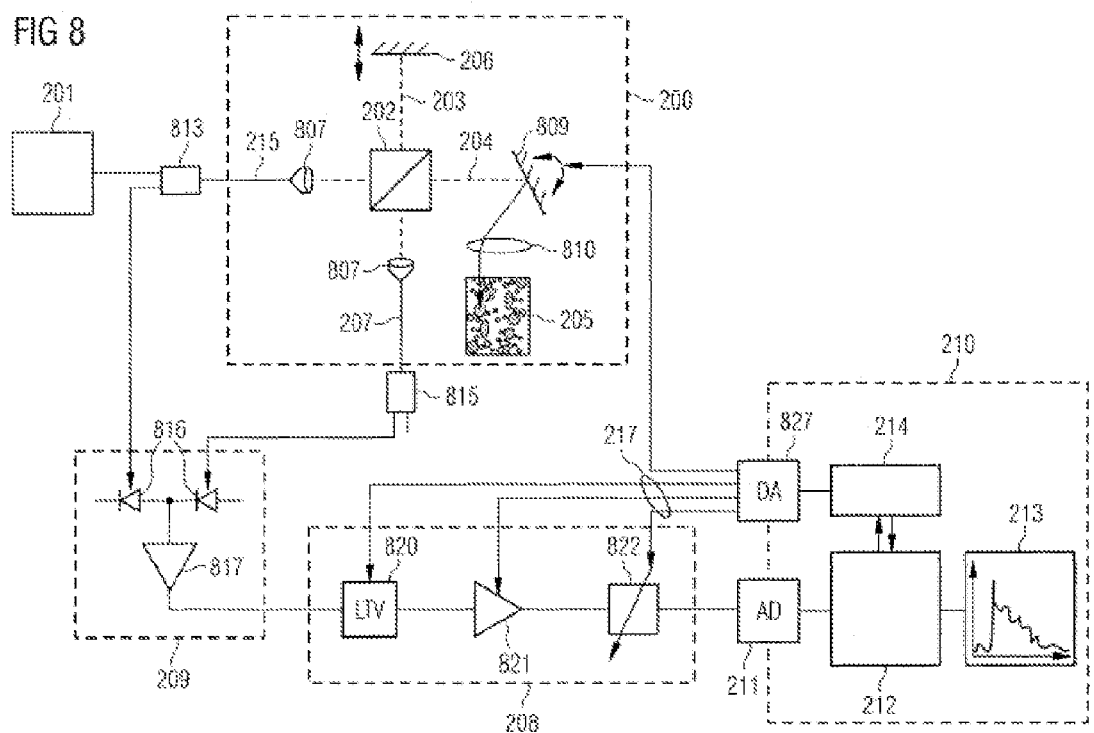
FIG. 8 shows a schematic structure of a system according to a sixth preferred embodiment of the disclosure.

A preferred exemplary embodiment for the implementation of the present invention will be described hereafter on the basis of a highly-dynamic TD-OCT system with reference to FIG. 8, in which an analog electrical signal processing unit 208 is arranged between a detector 209 and an A/D converter 211. The example is based on a Michelson interferometer 200 as a measurement interferometer. It comprises a semi-transmissive mirror 202 (as a beam splitter), an illumination arm 215, a sample arm 204, a reference arm 203, and a detection arm 207. The interferometer is preferably constructed with open beam optics. Two fiber collimators 807 are used for coupling the light beam in and out. A superluminescent diode as a white light source 201, having a spectral bandwidth of 110 nm and a middle wavelength of 1330 nm, is located in the illumination arm 215.

The sample arm 204 preferably comprises a beam deflection unit 809, consisting of two galvanometer scanning mirrors, one in each case for each transverse deflection direction. This is followed in the sample arm 204 by a scanning lens 810, which is adapted to the beam deflection unit and converts the deflection angle generated therein into a transverse offset. The scanning lens 810 is also used for focusing the collimated light beam into the sample 205. The reference arm 203 preferably comprises a displaceable reference reflector 206.

A differential reception scheme is applied in this exemplary embodiment. Therefore, the illumination arm 215 additionally fulfills the task of a second detection arm. The optical power is partially coupled out of the illumination arm 215 by means of a first 50-50 coupler 813 and supplied like the light from the detection arm 207 to the differential detector 209 for this purpose. To achieve equal signal intensities at both detector inputs, a second 50-50 coupler 815 is located in the detection arm. The differential receiver is constructed in particular from two photodiodes 816 connected in series and a trans-impedance amplifier 817. The optical power difference of both inputs is converted proportionally into a voltage signal at the output.

The analog signal processing unit 208 is located between detector and the analog/digital converter 211, which is implemented, for example, as a 16-bit A/D converter. It comprises in detail in particular a linear time-invariant element (LTV) 820, a low-noise amplifier 821, and a digital stepped damping member 822. In this case, the linear time-invariant element is preferably a variable electrical attenuator in this embodiment. The data acquisition and processing unit 210 preferably contains a numeric data evaluation module 212, a control module 214, and a data output unit 213. The numeric data evaluation module is used for processing the digitized signal. This includes in particular the reconstruction of the backscattering profile from the measurement data, the numeric correction of the influence of the analog signal processing, and the recognition of possible local overshoots of the dynamic range of the analog/digital converter 211. Such range overshoots can be recognized, for example, by multiple, successive values at the upper or lower edge of the dynamic range of the A/D converter.

The control module 214 has the task in particular of counteracting these range overshoots by control of the analog signal processing unit 208, in that the analog measurement signal is attenuated or amplified at the point of the local range overshoot or undershoot, respectively. The control module 214 also controls the numeric correction step, i.e., the digital compensation of the influence of the analog signal processing unit 208 by means of the data evaluation module 212, and the beam deflection unit in the sample arm 204. Control signals of the control module 214, which leave the data acquisition and processing unit 201, are preferably converted for this purpose by means of a digital/analog converter (D/A) 827.

Figure 9:
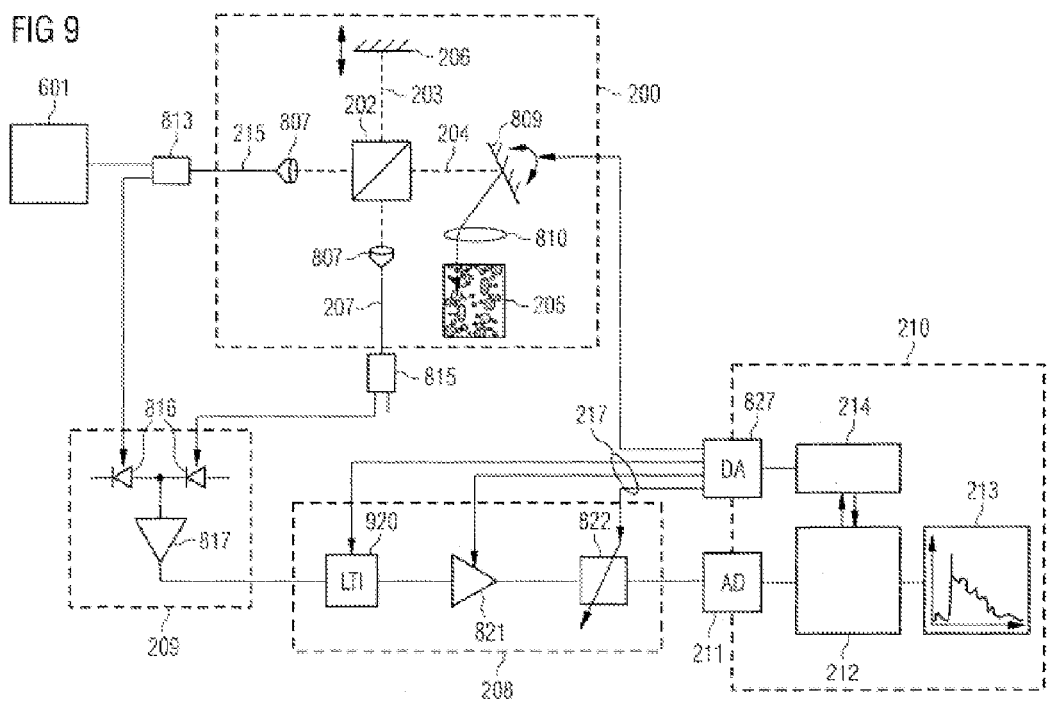
FIG. 9 shows a schematic structure of a system according to a seventh preferred embodiment of the disclosure.

A possible implementation of the invention in an SS-OCT system having expanded dynamic range according to a further preferred embodiment is shown in FIG. 9. A Michelson interferometer 200 is shown therein as a measurement interferometer. This comprises a semi-transmissive mirror 202 as a beam splitter, an illumination arm 215, a sample arm 204, a reference arm 203, and a detection arm 207. The interferometer is preferably constructed from free beam optics. Two fiber collimators 807 are used for coupling the light beam in and out. A swept source 601, tunable over a wavelength range from 1240 nm to 1380 nm, having a scanning rate of 20 kHz, for example, is located in the illumination arm 215. The sample arm 204 contains a beam deflection unit 809, which comprises in particular two galvanometer scanning mirrors, one in each case for each transverse deflection direction. This is followed in the sample arm 204 by a scanning lens 810, which is adapted to the beam deflection unit 809 and converts the deflection angle generated therein into a transverse offset. The scanning lens 810 is also used for focusing the collimated light beam into the following sample 205. The reference arm contains a fixedly positioned reference reflector 206.

A differential reception scheme is also applied in this exemplary embodiment. Therefore, the illumination arm 215 additionally fulfills the task of a second detection arm. The optical power is partially coupled out of the illumination arm 215 by means of a first 50-50 coupler 813 and supplied like the light from the detection arm to the differential detector 209 for this purpose. To achieve equal signal intensities at both detector inputs, a second 50-50 coupler 815 is located in the detection arm 207. The differential receiver is constructed in particular from two photodiodes 816 connected in series and a trans-impedance amplifier 817. The optical power difference of both inputs is converted proportionally into a voltage signal at the output.

The analog signal processing unit 208 is located between detector 209 and the analog/digital converter 211, which is implemented, for example, as a 12-bit converter. It comprises in detail in particular an adaptive filter unit (LTI) 920, a low-noise amplifier 821, and a digital stepped damping member 822. In this case, the adaptive filter unit is preferably constructed as a series circuit of a second-order LC-Butterworth high-pass filter, having limiting frequency of 200 kHz, and a notch filter having variable blocking frequency, and an active high-pass filter in Butterworth configuration with settable limiting frequency in the range from approximately 2 MHz to approximately 20 MHz.

The data acquisition and processing unit 210 comprises in particular a numeric data evaluation module 212, a control module 214, and a data output unit 213. The numeric data evaluation module is designed in particular for the Fourier transform and back-calculation of the measured signal for backscattering depths, including numeric correction of the analog signal processing and recognition of possible local overshoots of the dynamic range of the analog/digital converter 211. Such range overshoots can be recognized, for example, by way of multiple successive non-Fourier-transformed values at the upper edge of the dynamic range of the A/D converter or by multiple successive Fourier-transformed values at the lower noise limit of the system. This noise limit can be read at points of the depth scan at which no backscattering is expected, for example, on air.

The control module 214 is designed to counteract these range overshoots by control of the analog signal processing unit 208. For this purpose, the spectral filter characteristic is adapted and the amplification and damping properties of the amplification and damping member are adapted. For example, the frequency band in which the facet reflection appears is damped in a targeted manner. This adaptation process is preferably performed iteratively. The overall reflectivity profile is particularly preferably damped strongly enough that no overshoot of the dynamic range of the A/D converter 211 occurs on the upper end. This is checked before the Fourier transform. In the next step, a Fourier transform of the signal preferably occurs. The signal being provided shows which frequency fractions occur with greater power. The linear time-invariant filter 920 can subsequently be set so that the stronger frequency fractions are attenuated. In return, the overall power of the input signal is increased again, or the damping is reduced. If overshoots of the dynamic range of the A/D converter furthermore occur, the adaptation steps are repeated.

The control module 214 is preferably additionally designed to control the numeric compensation of the effect of the analog signal processing unit 209 in the data evaluation module 212 and the beam deflection unit 809 in the sample arm 204. Control signals which leave the data acquisition and processing unit 210 are converted for this purpose in a digital/analog converter (D/A) 827.

LIST OF REFERENCE NUMERALS 110 backscattering profile
111 increase
112 signal peak
113 exponentially decreasing profile of the backscattering
114 sample to be studied
115 conventional signal lower limit
116 lower limit of the measurement range
117 fundamental (analog) sensitivity limit
118 level of the quantification noise of the A/D converter
119 measurement range
120 dynamic range of the A/D converter
121 high-pass range
122 notch filter
123 high-pass characteristic increasing exponentially with frequency
124 weighting guideline
125 effective dynamics of the system
131 modified backscattering profile
140 reconstructed backscattering profile
141 depth-dependent measurement range
200 Michelson interferometer
201 broadband light source
202 beam splitter
203 reference arm
204 sample arm
205 sample
206 reference reflector
207 detection arm
208 adaptive analog signal processing unit
209 detector
210 data acquisition and processing unit
211 analog/digital converter
212 data evaluation module
213 data output unit
214 control module
215 illumination arm
216 analog measurement signal
217 control signal
601 tunable laser source
602 measurement interferometer
604 measurement signal
807 fiber collimator
809 beam deflection unit
810 scanning lens
813 optical coupler
815 optical coupler
816 photodiode
817 trans-impedance amplifier
820 linear time-invariant element
821 electrical amplifier
822 digital stepped damping member
827 digital/analog converter
920 linear time-invariant element

The invention claimed is:

1. A system for optical coherence tomography, comprising:
an optical detection unit (200, 201, 209) for the optical acquisition of a measurement-depth-dependent optical backscattering profile (110), wherein the optical detection unit (200, 201, 209; 601, 602, 209) is designed to generate an analog measurement signal (216) of the acquired measurement-depth-dependent optical backscattering profile (110), wherein the optical detection unit comprises a controllable analog signal processing unit (208), which is designed to perform selective weighting of the fractions of the analog measurement signal associated with various measurement depths in dependence on a detected control signal (217);
a signal converter unit (211), which is designed to acquire the analog measurement signal (216) of the optical detection unit and convert it into a digital signal; and
a data acquisition and processing unit (210), which is designed to ascertain overshoots and/or undershoots of a dynamic range of the signal converter unit (211), to control the analog signal processing unit by means of the control signal such that an ascertained overshoot and/or undershoot of the dynamic range of the signal converter unit is counteracted, and to perform a correction of the digital signal such that the weighting of various signal fractions performed by the signal processing unit is thus compensated for.

2. The system as claimed in claim 1, wherein the optical detection unit comprises:
a light source (601), the wavelength of which is chronologically variable within a scanning range of the optical detection unit; and
an optical detector (209), which is designed to convert an optical signal of the optical detection unit into an analog electrical measurement signal (604),
wherein the analog signal processing unit (208) comprises an adaptive linear time-invariant filter, which performs filtering of the electrical measurement signal.

3. The system as claimed in claim 2, wherein the adaptive filter comprises a high-pass filter hands/or a bandpass filter and/or a notch filter and/or a broadband amplification unit.

4. The system as claimed in claim 1, wherein the optical detection unit comprises an optical interferometer (200) having a sample arm (204) and a reference arm (203), wherein an optical path difference between the sample arm (204) and the reference arm (203) is chronologically variable to scan the measurement depth, and wherein the analog signal processing unit (208) comprises a chronologically variable linear amplification and/or damping element, which is controlled by the data acquisition and processing unit (210) in dependence on the optical path difference between the sample arm (204) and the reference arm (203).

5. The system as claimed in claim 4, wherein the amplification and/or damping member comprises an electrical amplification and/or damping member.

6. The system as claimed in claim 4, wherein the amplification and/or damping member comprises an optical amplification and/or damping member.

7. A method for optical coherence tomography comprising:
acquiring a measurement-depth-dependent optical backscattering profile by means of an optical detection unit, which generates an analog measurement signal;
converting the analog measurement signal into a digital signal by means of a signal converter unit (211);
ascertaining an overshoot and/or undershoot of a dynamic range of the signal converter unit (211);
selective weighting of the fractions of the analog measurement signal, which are associated with various measurement depths, by means of an adaptive analog signal processing unit (208) such that an ascertained overshoot and/or undershoot of the dynamic range is counteracted;

correcting the digital signal such that a weighting, which is performed by means of the analog signal processing unit, of various fractions of analog signal is thus compensated for.

8. The method as claimed in claim 7, wherein the acquisition of the optical backscattering profile, the generation of an analog measurement signal, and the ascertainment of an overshoot and/or undershoot of the dynamic range is firstly carried out for a first setting of the adaptive analog signal processing unit, wherein subsequently, in dependence on the ascertained overshoot and/or undershoot of the dynamic range, an adapted setting of the adaptive analog signal processing unit is performed, and wherein the acquisition of the optical backscattering profile, the generation of an analog measurement signal, and the ascertainment of an overshoot and/or undershoot of the dynamic range is repeated at a respectively adapted setting of the analog signal processing unit until a predefined interrupt criterion is fulfilled, and wherein a correction of the digital signal is performed according to a last setting of the analog signal processing unit.

9. A computer-implemented method for controlling an optical coherence tomography measurement, comprising
acquiring a digital signal, which is generated by a signal converter unit, of a measurement-depth-dependent backscattering profile of an optical coherence tomography measurement;
ascertaining an overshoot and/or undershoot of a dynamic range of the signal converter unit;
generating a control signal for controlling an adaptive analog signal processing unit such that a selective weighting, which is caused by the control signal of the adaptive analog signal processing unit, of analog signal fractions, which are associated with various measurement depths, of the backscattering profile of the optical coherence tomography measurement counteracts the ascertained overshoot and/or undershoot of the dynamic range; and
correcting the digital signal such that the selective weighting, which is performed by the signal processing unit, of various signal fractions is thus compensated for.

10. A computer system for controlling an optical coherence tomography measurement, comprising
a digital signal input for acquiring a digital signal, which is generated by a signal converter unit, of a measurement-depth-dependent backscattering profile of an optical coherence tomography measurement;
a data evaluation module for ascertaining an overshoot and/or undershoot of a dynamic range of the signal converter unit;
a data memory having a control guideline which, for overshoots and/or undershoots of the dynamic range of the signal converter unit, establishes values of a control signal for controlling an adaptive analog signal processing unit such that a selective weighting, which is caused by the control signal of the adaptive analog signal processing unit, of signal fractions, which are associated with various measurement depths, of the backscattering profile of the optical coherence tomography measurement counteracts the overshoots and/or undershoots of the dynamic range; and
a control module which generates a control signal the ascertained overshoot and/or undershoot of the dynamic range according to the control guideline stored in the data memory,
wherein the data evaluation module is designed to correct the digital signal such that the selective weighting of various signal fractions, which is caused by the signal processing unit according to the control guideline for the generated control signal, is thus compensated for.

* * * * *